United States Patent
Girard

(10) Patent No.: US 8,220,133 B2
(45) Date of Patent: Jul. 17, 2012

(54) METHOD FOR ATTACHING A CABLE TO THE HOUSING OF AN ELECTRONIC CIRCUIT

(75) Inventor: Frédéric Girard, Grenoble (FR)

(73) Assignee: E2V Semiconductors (FR)

( * ) Notice: Subject to any disclaimer, the term of this patent is extended or adjusted under 35 U.S.C. 154(b) by 409 days.

(21) Appl. No.: 12/594,033

(22) PCT Filed: Apr. 14, 2008

(86) PCT No.: PCT/EP2008/054475
§ 371 (c)(1),
(2), (4) Date: Dec. 1, 2009

(87) PCT Pub. No.: WO2008/135342
PCT Pub. Date: Nov. 13, 2008

(65) Prior Publication Data
US 2010/0107398 A1    May 6, 2010

(30) Foreign Application Priority Data
Apr. 17, 2007   (FR) ..................... 07 02780

(51) Int. Cl.
*B23P 19/02*    (2006.01)
(52) U.S. Cl. .......... 29/525; 29/447; 29/527.1; 29/564.4; 29/854; 29/876; 439/578
(58) Field of Classification Search ............. 29/854, 29/857–859, 876, 883, 564.4, 447, 527.1; 439/578
See application file for complete search history.

(56) References Cited

U.S. PATENT DOCUMENTS

| | | | | |
|---|---|---|---|---|
| 5,305,406 A * | 4/1994 | Rondeau | ...................... | 385/81 |
| 5,691,539 A * | 11/1997 | Pfeiffer | .................... | 250/370.09 |
| 6,030,119 A * | 2/2000 | Tachibana et al. | ............ | 378/169 |
| 6,848,939 B2 * | 2/2005 | Stirling | ........................ | 439/578 |
| 7,297,023 B2 * | 11/2007 | Chawgo | ........................ | 439/578 |
| 7,331,820 B2 * | 2/2008 | Burris et al. | ................. | 439/578 |
| 7,635,283 B1 * | 12/2009 | Islam | ........................... | 439/583 |
| 7,857,661 B1 * | 12/2010 | Islam | ........................... | 439/584 |
| 7,931,498 B2 * | 4/2011 | Skeels et al. | ................. | 439/578 |
| 7,950,957 B1 * | 5/2011 | Yang | ............................ | 439/578 |

(Continued)

FOREIGN PATENT DOCUMENTS

| | | |
|---|---|---|
| EP | 1699232 | 9/2006 |
| JP | 2000023973 | 1/2000 |

*Primary Examiner* — Derris Banks
*Assistant Examiner* — Azm Parvez
(74) *Attorney, Agent, or Firm* — Lowe Hauptman Ham & Berner, LLP

(57) ABSTRACT

The invention relates to the attachment of a multiple-conductor electronic cable to an electronic circuit in a sealed housing. The cable is placed in a sheath of a heat-deformable material and the method comprises the following steps: placing a rigid bushing (40) with a protruding collar (48) on the exposed end of the cable, heating the end in a conical mold or softening the sheath, inserting the bushing between the cable conductors and the softened sheath, the collar of the bushing pushing the sheath material until the conical portion of the mold is filled, cooling the sheath for solidifying it, extracting the end of the cable from the mold, the end having a conical portion with an increasing diameter ending with the protruding collar, inserting the cable in the housing opening from the inside before closing the housing. The invention can be used or an intra-oral dental radiology sensor.

18 Claims, 3 Drawing Sheets

U.S. PATENT DOCUMENTS

| | | | |
|---|---|---|---|
| 7,950,958 B2 * | 5/2011 | Mathews | 439/578 |
| 7,976,339 B2 * | 7/2011 | Buck et al. | 439/578 |
| 2006/0110977 A1 * | 5/2006 | Matthews | 439/578 |
| 2007/0081358 A1 | 4/2007 | Shea et al. | |

* cited by examiner

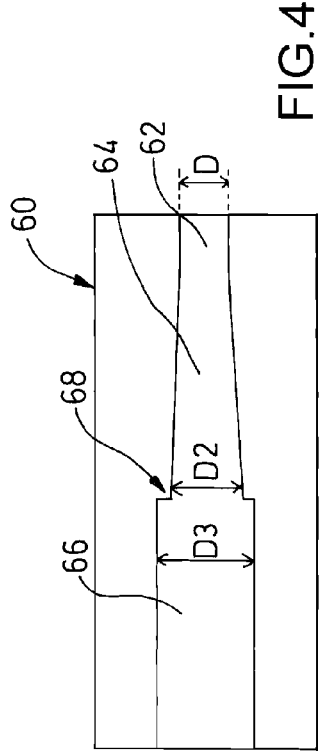
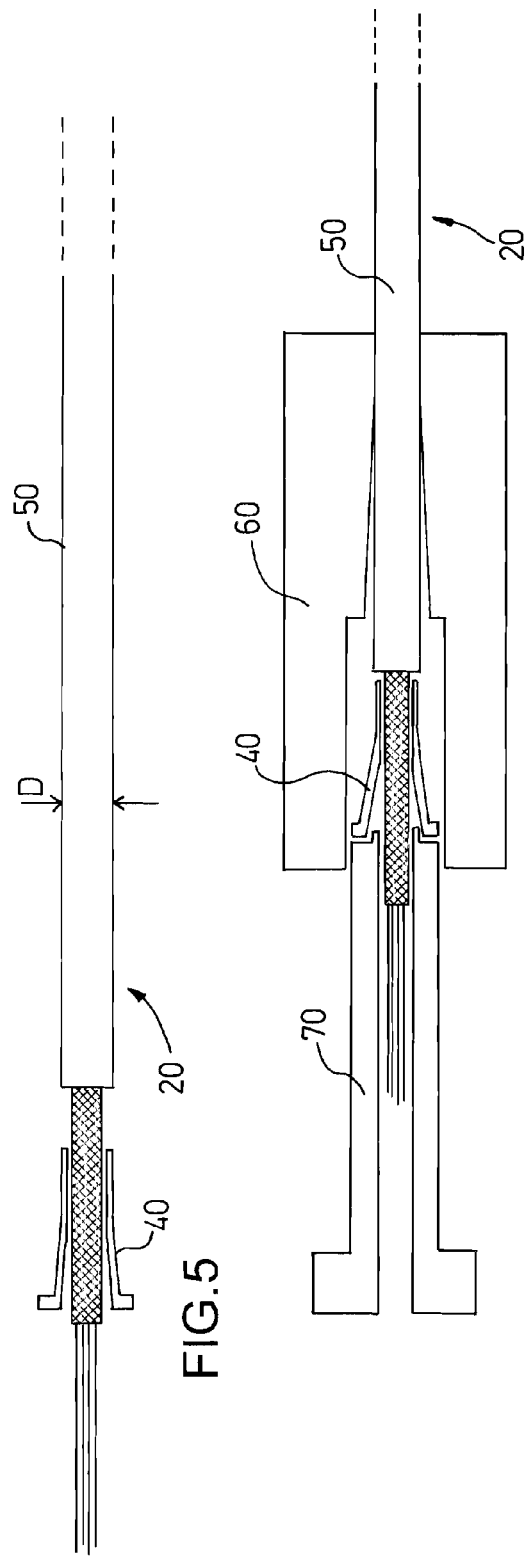

METHOD FOR ATTACHING A CABLE TO THE HOUSING OF AN ELECTRONIC CIRCUIT

CROSS-REFERENCE TO RELATED APPLICATIONS

The present Application is based on International Application No. PCT/EP2008/054475, filed on Apr. 14, 2008, which in turn corresponds to French Application No. 0702780, filed on Apr. 17, 2007, and priority is hereby claimed under 35 USC §119 based on these applications. Each of these applications are hereby incorporated by reference in their entirety into the present application.

FIELD OF THE INVENTION

The invention relates to the attachment of a multiple-conductor electronic cable to an electronic circuit contained in a sealed housing.

The invention will be described in conjunction with the attachment of a cable to an intra-oral dental radiology sensor although it can also be applied to other scenarios.

BACKGROUND OF THE INVENTION

It is important that the attachment of the cable be highly resistant to being pulled out, and also to the twisting of the cable on itself, repeated bending, and the risk of the cable being bent with too small a bend radius about its attachment. It is also important to provide sealing in contexts where there is a risk of ingress of moisture (or of any other gaseous or liquid corrosive atmosphere) into the housing, as is the case, for example, of a radiological sensor placed in the mouth of a patient.

It is not easy to design methods of attaching cables which allow all these constraints to be satisfied optimally.

In the prior art, a cable attachment was often reinforced by overmolding flexible plastic around the cable outlet, this overmolding encompassing both part of the cable and part of the housing. The problem with this overmolding was that it was bulky.

It is an object of the present invention to provide a method of manufacture that is more effective than those proposed hitherto for improving the robustness and other qualities (such as the sealing) of the attachment without thereby increasing the bulk thereof, bulk being critical in certain applications.

In order to achieve this, the invention proposes a method of attaching an electric cable, covered with a sheath made of a thermodeformable plastic, to an electronic circuit housing. A rigid bushing is fitting onto the stripped end of the cable having a hollow body, the inside diameter of which accepts the conductors but not the sheath of the cable. The bushing has a protruding collar at its end. The end of the cable and the bushing is fitted into a heated mold comprising a slightly conical interior surface part of a diameter smaller than that of the collar and a cylindrical part of a diameter larger than the large diameter of the conical part. The mold is heated to a temperature at which the material of the sheath will soften. The bushing is driven in the direction of the axis of the cable, so that the body of the bushing becomes inserted between the conductors of the cable that it surrounds and the softened sheath. The collar of the bushing is upset so that the material of the sheath to the point it fills the conical part of the mold. In order to solidify the sheath, it is cooled. The end of the cable is extracted from the mold. The end has a conical sheath portion of increasing diameter ending with the protruding collar. Another end of the cable is inserted, from inside the housing, through an opening in the housing, the diameter of which is very slightly smaller than the largest diameter of the conical sheath portion. The housing is closed.

SUMMARY OF THE INVENTION

What is meant by the fact that the mold has a "slightly conical shape" is that the half cone angle does not exceed 0.1 radians or even, for preference, 0.05 radians.

The bushing is preferably made of a hard plastic such as nylon; it also preferably has a conical shape or a conical shape extended by a cylindrical part. Its exterior surface is preferably ribbed to exhibit annular peripheral grooves that improve the pull-out strength. A second conical bushing, preferably made of brass, may be inserted between the first bushing and the conductors of the cable; this second bushing makes it possible to maintain the taper of the first bushing during and after molding and plays a part in the electrical grounding of a metal shielding braid when the cable has such a braid.

For preference, while the first bushing is being molded and driven into the softened sheath, the collar of the bushing presses the end of the sheath against a step between the cylindrical part and the conical part of the mold, thus forming, at the end of the cable, a plastic collar which adds to the collar of the bushing.

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious aspects, all without departing from the invention. Accordingly, the drawings and description.

BRIEF DESCRIPTION OF THE DRAWINGS

The present invention is illustrated by way of example, and not by limitation, in the figures of the accompanying drawings, wherein elements having the same reference numeral designations represent like elements throughout and wherein:

FIG. 3 is a perspective view of a bushing that is partly cylindrical and partly conical, intended to be inserted between the conductors of the cable and the sheath during manufacture;

FIG. 4 is a cross section of the heated mold intended to shape the end of the cable;

FIG. 5 depicts one step in the fitting of the bushing on the stripped end of the cable;

FIG. 6 depicts the start of a step of driving the bushing into the mold;

DESCRIPTION OF PREFERRED EMBODIMENTS

Figure 1:
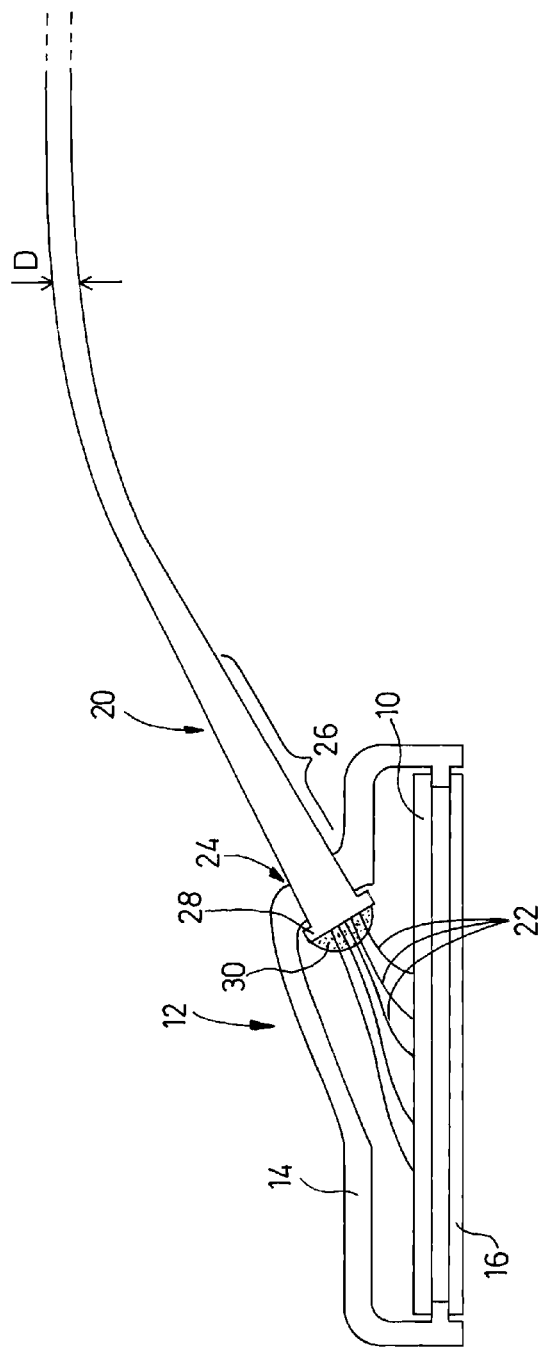
FIG. 1 depicts an overview of an electronic circuit housing connected to a multiple-strand cable using the method according to the invention.

The invention will be described by way of example in connection with an intra-oral X-ray imaging sensor visible in FIG. 1. The X-ray imaging electronic circuit is symbolized by a printed circuit board 10 to which various components not depicted, and notably an X-ray imaging integrated circuit chip, are attached in the conventional way.

The electronic circuit is mounted in a housing 12 comprising a cap 14 and a blanking plate 16. The cap and the blanking plate may be made of plastic or of composite resin or of metal.

The connection between the electronic circuit and the outside is provided by a multiple-strand cable 20, the conducting wires 22 of which are soldered to the electronic circuit 10 inside the housing. The wires are enclosed in a sheath made of thermodeformable plastic (preferably polyurethane). This sheath passes through an opening 24 made in the cap 14 of the housing. The wires leave the end of the sheath longitudinally, inside the housing.

The cable sheath has a diameter which is generally constant D, except at the end where it is connected to the housing. At this end, the sheath widens into a slightly conical shape in a region 26: its diameter increases as it nears the end of the cable and therefore as it nears the opening 24 in the housing. The natural diameter of the sheath at the point at which it is held in the opening 24 is very slightly greater than the diameter of the opening (for example one tenth of a millimeter greater); during fitting, the sheath is forced into the opening, its natural elasticity allowing it through; once it has been fitted, the sheath is pressed very closely against this opening around its entire periphery, providing sealing between the inside and the outside of the housing.

The end of the cable comprises a protruding collar 28, of a diameter larger than the diameter of the opening 24 so that the cable cannot leave the opening even under the effect of a strong pulling force from the outside. A dome 30 of hard adhesive may terminate the sheathed part of the cable; the conducting wires 22 are held in position by the dome and leave it to be soldered to the electronic circuit 10.

Figure 2:
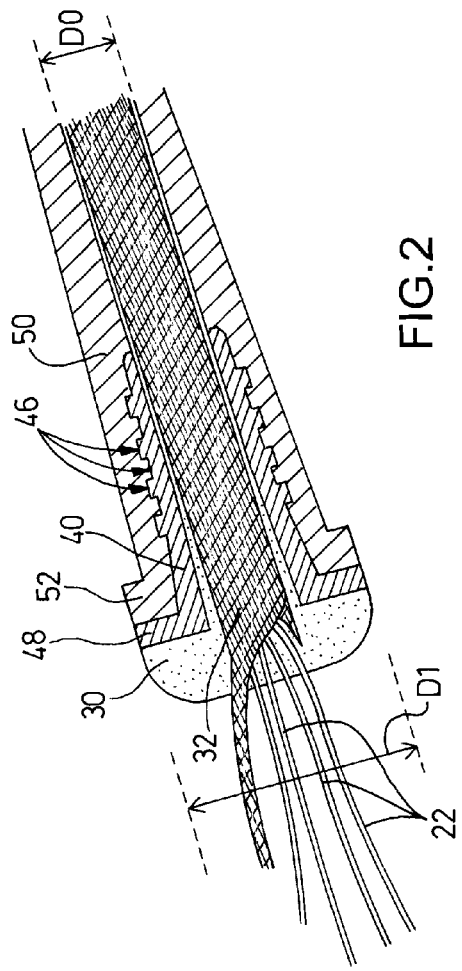
FIG. 2 is a detailed cross-sectional view of the end of the cable.

FIG. 2 depicts the structure of the conical end of the cable in greater detail.

The cable is depicted as having several wires 22 surrounded overall by a shielding braid 32, although this braid is not compulsory. The wires 22 may be coated with an insulating layer which is stripped off only at the site (not depicted) of the soldered connection with the electronic circuit.

A rigid bushing 40, preferably made of hard plastic such as nylon, surrounds the conducting wires 22 and the braid 32 and is itself surrounded by the sheath 50 made of thermodeformable plastic. The bushing 40 preferably comprises ribs in the form of recesses and protrusions which anchor it into the sheath 50, increasing the resistance of the bushing to being pulled out of the sheath (in the longitudinal direction of the cable). The ribs are preferably in the form of circular annuli around the bushing. They preferably have a width (width of the recesses or width of the protrusions) of 0.2 to 0.5 millimeters and a depth of 0.2 to 0.5 millimeters.

The dome of adhesive 30 helps to secure the bushing and the sheath to one another while at the same time holding the conductors 22 in place.

Figure 10:
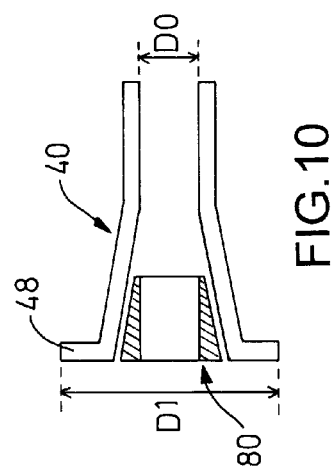
FIG. 10 depicts a configuration with two bushings, one made of plastic and the other of brass.

The bushing 40, also visible in FIG. 3 and, in another form, in FIG. 10, is a hollow body which preferably has a cylindrical part 42 (at the end driven most deeply into the cable sheath) and a conical part 44 (at the end closest to the end of the cable). The conical part widens from the cylindrical part toward the outside of the cable. It will be seen later on (in FIG. 10) that, in one particular configuration, a second conical bushing may be inserted between the first bushing 40 and the shielding braid 32.

The material of the bushing 40 does not have to be thermodeformable at the softening temperature of the material of which the cable sheath is formed.

The bushing preferably has, on the side of the cylindrical part 42, a small inside diameter D0 barely greater than the diameter of the stripped cable but smaller than the diameter D of the sheath, so that the stripped cable can enter the bushing but the sheath cannot.

The bushing preferably ends in a protruding annular collar 48 of diameter D1 greater than the outside diameter of the conical part 44. The protrusion may be by about 1 millimeter.

The collar 48 of the bushing is preferably supplemented by a protruding collar 52 of the sheath 50, of a diameter greater than the largest diameter of the conical part of the sheath. This sheath collar 52, reinforced by the bushing collar 48, presses against the rim of the opening 24 in the housing (FIG. 1), on the inside thereof, when the cable is in place. The diameter of the collar 52 of the sheath is, in principle, equal to the diameter D1 of the collar of the bushing.

FIG. 4 depicts the mold used to shape the end of the cable. This is a heated mold able to raise the end of the cable to a temperature at which the plastic that forms the sheath 50 softens.

The mold 60 is depicted in a closed state; the mold is preferably one that can open in two parts, although this is not compulsory given its shape with one side fairly open.

The mold preferably comprises:
  a cylindrical interior surface part 62, preferably smooth, of a small diameter equal to the diameter D of the sheath of the cable in its non-widened part;
  a conical interior surface part 64, intended to shape the end of the cable, widening slightly from the part 62 and reaching a diameter D2 greater than D; the diameter D2 is very slightly greater (for example one tenth of a millimeter greater) than the diameter of the opening 24 of the housing but less (about 2 millimeters less) than the diameter D1 of the collar of the bushing so that the collar cannot enter this conical part; the conical surface 64 is preferably smooth;
  a cylindrical interior surface part 66 of a diameter D3 greater than D2, with a step 68 of a height measuring (D3−D2)/2 (about 1 millimeter) between the cylindrical part 66 and the conical part 64; the diameter D3 is greater than or equal to (preferably very slightly greater than) the diameter D1 of the collar 48 of the rigid bushing 40 so that the collar can enter the cylindrical part 66.

The half cone angle is preferably less than 0.05 radians (about) 3°. The length is a few centimeters, for a cable with an outside diameter of a few millimeters.

FIG. 5 shows the initial steps in the method of manufacture according to the invention: the starting point is a cable 20 with a sheath 50 of thermodeformable material of uniform diameter D; a first end of the cable (on the left in FIG. 5) is stripped; the bushing 40 is slipped via the small diameter thereof onto the stripped end (here, over the top of the braid of the cable), the bushing coming to butt against the sheath 50.

The cable end provided with the bushing is placed inside the mold 60 (FIG. 6).

The cable is fitted in such a way that part of the sheath is situated in the cylindrical part 66 of diameter D3. It is held firmly in the other cylindrical part 62 of diameter D.

The mold is heated to a softening temperature of the material of the sheath. The small end of the bushing 40 is driven into the softened sheath using a piston 70 which presses against the collar 48 of the bushing. The piston 70 is provided with an opening to accept the end of the conductors of the cable so that the piston does not push the conductors of the cable at the same time as it pushes the bushing.

Figure 7:
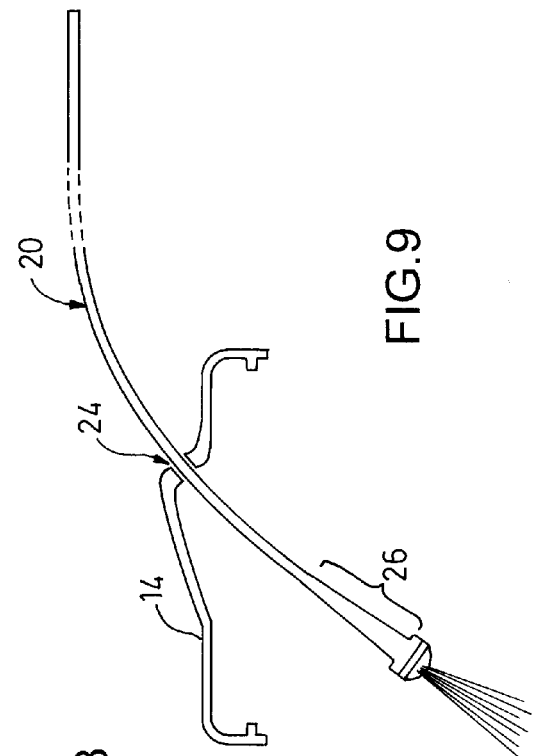
FIG. 7 depicts the end of the step of driving the bushing into the mold.

FIG. 7 depicts the end of the process of driving the bushing into the softened sheath. The material of the sheath has been upset by the collar of the bushing until it fills all of the conical part of the mold surrounding the body of the bushing, and any sheath material that is in excess of this conical part forms a collar of plastic, pressed by the collar of the bushing against the step 68 of the mold. If the diameter of the collar of the bushing is D1 very close to the diameter D3 of the mold, the collar of plastic of the sheath will have practically the same diameter (D1) as the bushing, as may be seen in FIG. 2.

Figure 8:
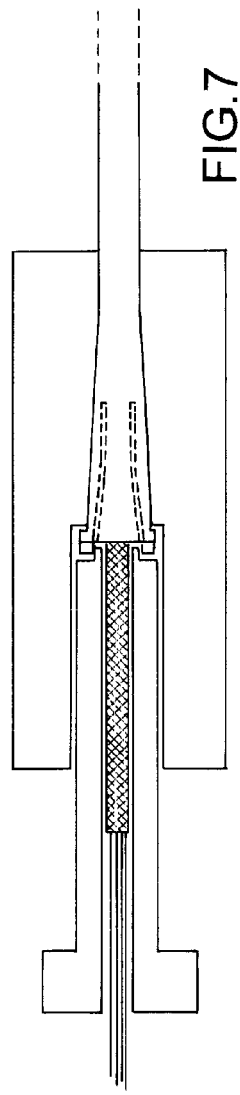
FIG. 8 depicts the extraction of the end of the cable from the mold.
Figure 9:
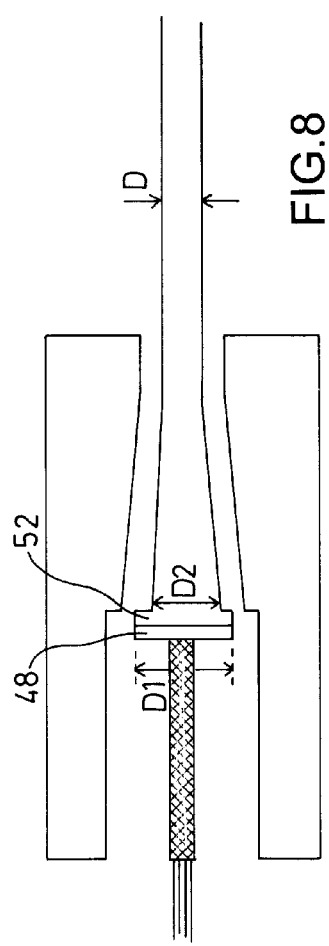
FIG. 9 depicts the insertion of the other end of the cable into the opening in the electronic circuit housing.

The mold is then cooled to solidify the sheath thus deformed, then the cable end is extracted from the mold. FIG. 8 shows this extraction in the case of an opening two-part mold, which is the simplest form to implement.

The cable then comprises a widened first end terminating in a double collar 48, 52. The small diameter of the widened part is the original diameter D of the cable. The large diameter is the large diameter D2 of the conical interior surface 64 of the mold, and the diameter of the collar is D1 for the bushing, D3 almost equal to D1 for the sheath. Apart from the protrusion formed by the collar, the cable is smooth, which is beneficial from the point of view of cleaning.

The second end of the cable (the end that has not been shaped by the mold) is inserted through the opening 24 from the inside of the electronic circuit housing. The cable is pulled, forcibly driving the widened part of the sheath (diameter D2) into the opening 24 (slightly smaller than D2) until the collar (48, 52) of the sheath is pressed against the interior rim of the opening 24. Because of this forcible driving, the widened part of the sheath makes the desired seal within the opening 24.

The conductors are soldered to the electronic circuit if that has not already been done prior to insertion.

The housing is hermetically sealed, for example by bonding the blanking plate 16 in position (FIG. 1).

In the above described embodiment, the bushing 40 has a conical part 44, and this conical part is conical both on its exterior surface (in contact with the sheath) and on its interior surface (surrounding the stripped cable). In this case, provision may be made for there to be a rigid second bushing, conical in shape on the outside but cylindrical on the inside, to be inserted into the conical part of the first bushing in order to maintain the conical shape thereof. FIG. 10 depicts this two-bushings assembly. The second bushing 80 has an inside diameter DO just greater than the diameter of the stripped cable, and an exterior surface cone angle corresponding to the cone angle of the interior surface of the first bushing. It is preferably made of brass and, if the cable has a metal shield braid surrounding the other conductors, the bushing comes into contact with this braid and may encourage the grounding of this braid; for example if a conducting wire intended to be soldered to the electronic circuit is inserted between the two bushings.

It will be readily seen by one of ordinary skill in the art that the present invention fulfils all of the objects set forth above. After reading the foregoing specification, one of ordinary skill in the art will be able to affect various changes, substitutions of equivalents and various aspects of the invention as broadly disclosed herein. It is therefore intended that the protection granted hereon be limited only by definition contained in the appended claims and equivalents thereof.

The invention claimed is:

1. A method of attaching an electric cable, covered with a sheath made of a thermodeformable plastic, to an electronic circuit housing, comprising the following steps:
    stripping one end of the cable and fitting onto the stripped end of the cable a rigid bushing comprising a hollow body, the inside diameter of which accepts the conductors but not the sheath of the cable, the bushing having one end provided with a protruding collar,
    fitting the one end of the cable and the one end of the bushing into a heatable mold comprising a slightly conical interior surface part of a diameter smaller than that of the collar and a cylindrical part of a diameter larger than the largest diameter of the conical part,
    heating the mold to a temperature at which the material of the sheath will soften,
    driving the bushing in the mold, in the direction of the axis of the cylindrical part, so that the body of the bushing becomes inserted between the conductors of the cable and the softened sheath, the collar of the bushing upsetting the thermodeformable plastic of the sheath to the point that it fills the conical part of the mold,
    cooling, in order to solidify the sheath, extracting said one end of the cable from the mold, said one end having a conical sheath portion of increasing diameter ending with the protruding collar,
    inserting another end of the cable, from inside the housing, through an opening in the housing, the diameter of which is very slightly smaller than the largest diameter of the conical sheath portion, and
    closing the housing.

2. The method as claimed in claim 1, wherein the bushing is ribbed to improve the resistance of the cable to being pulled out in the longitudinal direction thereof.

3. The method as claimed in claim 1, wherein the bushing is made of nylon.

4. The method as claimed in claim 1, wherein the bushing comprises a conical part terminated at its largest-diameter end by the collar.

5. The method as claimed in claim 4, wherein the conical part of the bushing is conical on the outside and on the inside, and a second bushing, of conical shape on the outside and which is cylindrical on the inside, is inserted inside the first bushing.

6. The method as claimed in claim 5, wherein the second bushing is made of brass.

7. The method as claimed in claim 1, wherein the sheath of the cable is made of polyurethane.

8. The method as claimed in claim 1, wherein the diameter of the cylindrical part of the mold is approximately 2 millimeters larger than the largest diameter of the conical part of the mold.

9. The method as claimed in claim 1, wherein, while the bushing is being driven into the softened sheath, the collar presses the end of the sheath against a step between the cylindrical part and the conical part of the mold, thus forming a plastic collar at the end of the cable.

10. The method as claimed in claim 1, wherein the interior surface of the conical part of the mold is smooth.

11. The method as claimed in claim 2, wherein the bushing comprises a conical part terminated at its largest-diameter end by the collar.

12. The method as claimed in claim 3, wherein the bushing comprises a conical part terminated at its largest-diameter end by the collar.

13. The method as claimed in claim 2, wherein the diameter of the cylindrical part of the mold is approximately 2 millimeters larger than the largest diameter of the conical part of the mold.

14. The method as claimed in claim 2, wherein, while the bushing is being driven into the softened sheath, the collar presses the end of the sheath against a step between the cylindrical part and the conical part of the mold, thus forming a plastic collar at the end of the cable.

15. The method as claimed in claim 11, wherein the conical part of the bushing is conical on the outside and on the inside, and a second bushing, of conical shape on the outside and which is cylindrical on the inside, is inserted inside the first bushing.

16. The method as claimed in claim 12, wherein the conical part of the bushing is conical on the outside and on the inside, and a second bushing, of conical shape on the outside and which is cylindrical on the inside, is inserted inside the first bushing.

17. The method as claimed in claim 13, wherein the conical part of the bushing is conical on the outside and on the inside, and a second bushing, of conical shape on the outside and which is cylindrical on the inside, is inserted inside the first bushing.

18. The method as claimed in claim 14, wherein the conical part of the bushing is conical on the outside and on the inside, and a second bushing, of conical shape on the outside and which is cylindrical on the inside, is inserted inside the first bushing.

* * * * *